United States Patent
Moriyasu et al.

(10) Patent No.: US 8,415,631 B2
(45) Date of Patent: Apr. 9, 2013

(54) TOF-PET APPARATUS, DETECTOR RING AND DETECTOR

(75) Inventors: Kenta Moriyasu, Nasushiobara (JP); Takuzo Takayama, Utsunomiya (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 19 days.

(21) Appl. No.: 13/161,689

(22) Filed: Jun. 16, 2011

(65) Prior Publication Data

US 2011/0309256 A1 Dec. 22, 2011

(30) Foreign Application Priority Data

Jun. 16, 2010 (JP) ................................. 2010-137732

(51) Int. Cl.
*G01T 1/164* (2006.01)
(52) U.S. Cl. .............................. 250/363.03; 250/363.04
(58) Field of Classification Search .............. 250/363.03
See application file for complete search history.

(56) References Cited

U.S. PATENT DOCUMENTS 5,015,861 A * 5/1991 Derenzo et al. ........... 250/361 R
5,813,983 A * 9/1998 DiFilippo et al. ............. 600/407
2004/0159792 A1 * 8/2004 Andreaco et al. ........ 250/363.03

FOREIGN PATENT DOCUMENTS

JP 2009-42029 2/2009

* cited by examiner

*Primary Examiner* — David Porta
*Assistant Examiner* — Marcus Taningco
(74) *Attorney, Agent, or Firm* — Oblon, Spivak, McClelland, Maier & Neustadt, L.L.P.

(57) ABSTRACT

According to one embodiment, a TOF-PET apparatus includes a plurality of detector rings arranged along a central axis thereof. Each of the detector rings comprises a plurality of scintillators and a plurality of photomultipliers. The scintillators are arranged on a substantial circumference around the central axis and generate scintillation in response to pair annihilation gamma-rays from a subject. The photomultipliers generate an electric signal in accordance with the generated scintillation. A length of each of the scintillators along a radial direction of the substantial circumference is set to a range in which a value of a total number of counts/time resolution of coincidence events of pair annihilation gamma-rays is more improved than when a reference scintillator whose probability of interaction with pair annihilation gamma-rays is adjusted to 80% is used under conditions of a constant total volume of the scintillators.

11 Claims, 7 Drawing Sheets

| Scintillator thickness (mm) | 6 | 8 | 10 | 12 | 14 | 16 | 18 | 24 |
|---|---|---|---|---|---|---|---|---|
| Scintillator time resolution (ps) | 266.5 | 270 | 276 | 269 | 294 | 318 | 315 | 331 |
| System time resolution (ps) | 481 | 483 | 486 | 482 | 496 | 511 | 509 | 519 |
| Total number of counts of coincidence events | 12500 | 17451 | 20760 | 23254 | 23512 | 23410 | 23066 | 22149 |
| Number of columns | 160 | 120 | 96 | 80 | 69 | 60 | 53 | 40 |
| Length in Z direction (mm) | 640 | 480 | 384 | 320 | 274 | 240 | 213 | 160 |
| Total number of counts / time resolution | 46.9 | 64.6 | 75.2 | 86.4 | 80.0 | 73.6 | 73.2 | 66.9 |
| Relative S / N ratio | 0.70 | 0.97 | 1.12 | 1.29 | 1.20 | 1.10 | 1.09 | 1.00 |

TOF-PET APPARATUS, DETECTOR RING AND DETECTOR

CROSS-REFERENCE TO RELATED APPLICATIONS

This application is based upon and claims the benefit of priority from Japanese Patent Application No. 2010-137732, filed Jun. 16, 2010; the entire contents of which are incorporated herein by reference.

FIELD

Embodiments described herein relate generally to a TOF-PET apparatus, a detector ring, and a detector.

BACKGROUND

A nuclear medicine diagnostic apparatus includes a detector ring composed of a plurality of detectors arranged in a ring shape. The nuclear medicine diagnostic apparatus detects radiation emitted from a subject to which a radioisotope is administered by detectors in the detector ring. A typical apparatus of this kind is a PET (Positron Emission computed Tomography) apparatus. Particularly, technology development of a TOF (Time of Flight)-PET apparatus is active. The TOF-PET apparatus uses a detection time difference of a pair of annihilation gamma-rays for image reconstruction. Thus, time resolution is very important for the TOF-PET apparatus.

A detector of the TOF-PET apparatus contains a scintillator formed from a scintillator material such as LYSO, LSO, and LGSO. The length of a scintillator of a detector ring along the radial direction, that is, the thickness of a scintillator is set to exceed 20 mm. This is because the mean free path of annihilation gamma-rays within the scintillator is taken into consideration. The mean free path is an average migration length of pair annihilation gamma-rays between the time when annihilation gamma-rays enter a scintillator and the time when an interaction with the scintillator is caused (when scintillation is generated). The scintillator is set to a thickness exceeding 20 mm to obtain adequate detection efficiency of gamma rays.

However, with an increasing thickness of the scintillator, variations in interaction position of annihilation gamma-rays along the depth direction inside the scintillator increase. With increasing variations in interaction position along the depth direction, the time resolution of a TOF-PET apparatus deteriorates. With a deteriorating time resolution, image quality declines. Moreover, the scintillator is expensive. Therefore, if the thickness of the scintillator increases, the amount of scintillator used in the TOF-PET apparatus increases and manufacturing costs of the TOF-PET apparatus also rise.

Compared with a non-TOF-PET apparatus, a TOF-PET apparatus can obtain clinically sufficient image quality with a smaller number of counts so that the examination time can be reduced. Therefore, dynamic imaging is expected as a useful clinical application of the TOF-PET apparatus. However, if the number of columns of a detector ring is increased to increase the size of the field of view, the amount of scintillator increases, leading to higher manufacturing costs.

DETAILED DESCRIPTION

In general, according to one embodiment, a TOF-PET apparatus includes a plurality of detector rings arranged along a central axis thereof. Each of the plurality of detector rings includes a plurality of scintillators arranged on a substantial circumference around the central axis to generate scintillation in response to pair annihilation gamma-rays from a subject and a plurality of photomultipliers that generates an electric signal in accordance with the generated scintillation. The length of each of the plurality of scintillators along the radial direction of the substantial circumference is set to a range in which the value obtained by dividing the total number of counts of coincidence events of pair annihilation gamma-rays by the time resolution is more improved than when a reference scintillator whose probability of interaction with annihilation gamma-rays is adjusted to 80% is used under conditions of a constant total volume of the scintillators.

The TOF-PET apparatus according to the present embodiment will be described in detail below with reference to the drawings.

Figure 1:
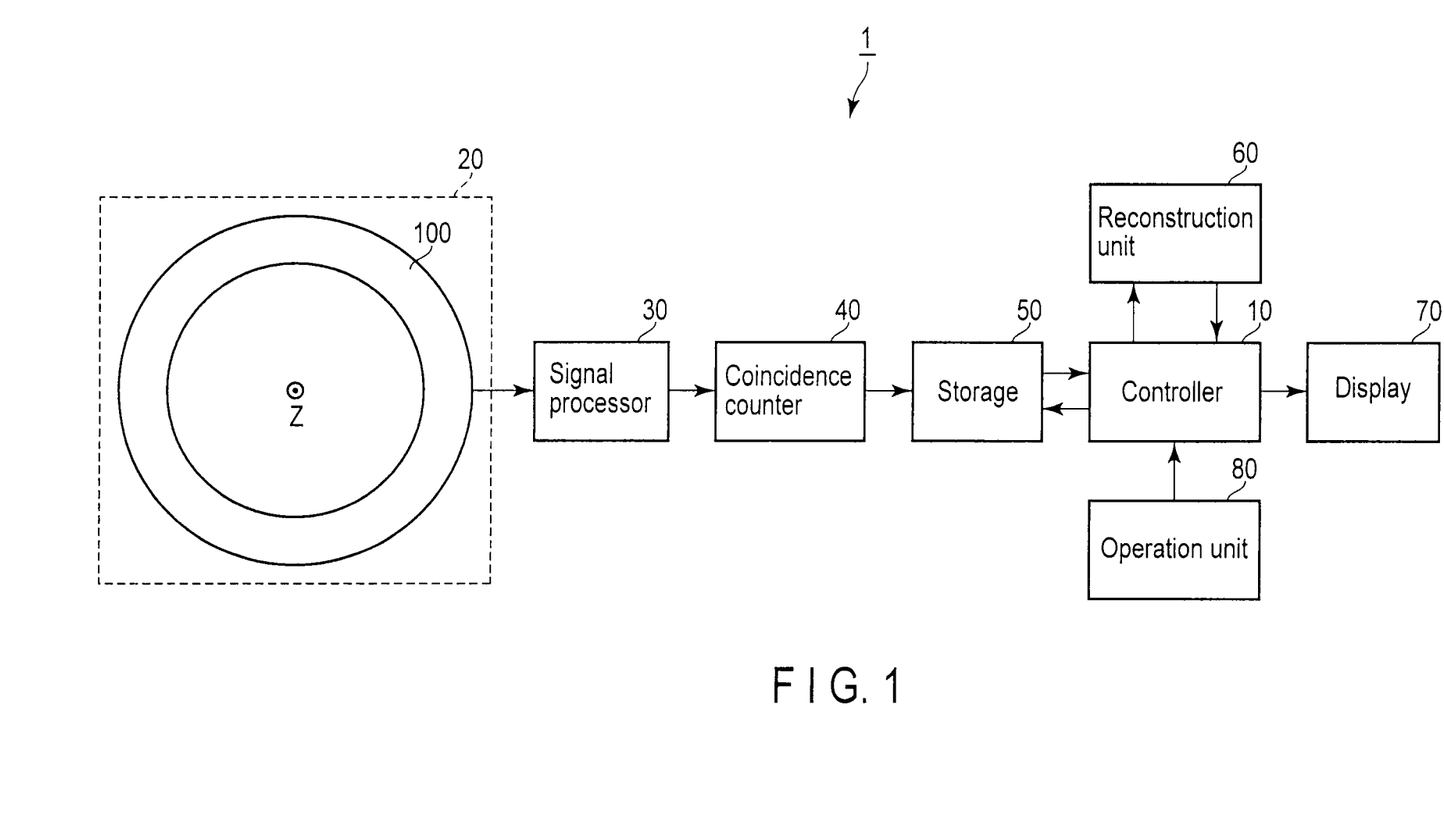
FIG. 1 is a diagram showing the configuration of a TOF-PET apparatus according to the present embodiment.

FIG. 1 is a diagram showing the configuration of a TOF-PET apparatus 1 according to the present embodiment. As shown in FIG. 1, the TOF-PET apparatus 1 includes a gantry 20, a signal processor 30, a coincidence counter 40, a storage 50, a reconstruction unit 60, a display 70, and an operation unit 80 around a controller 10.

Figure 2:
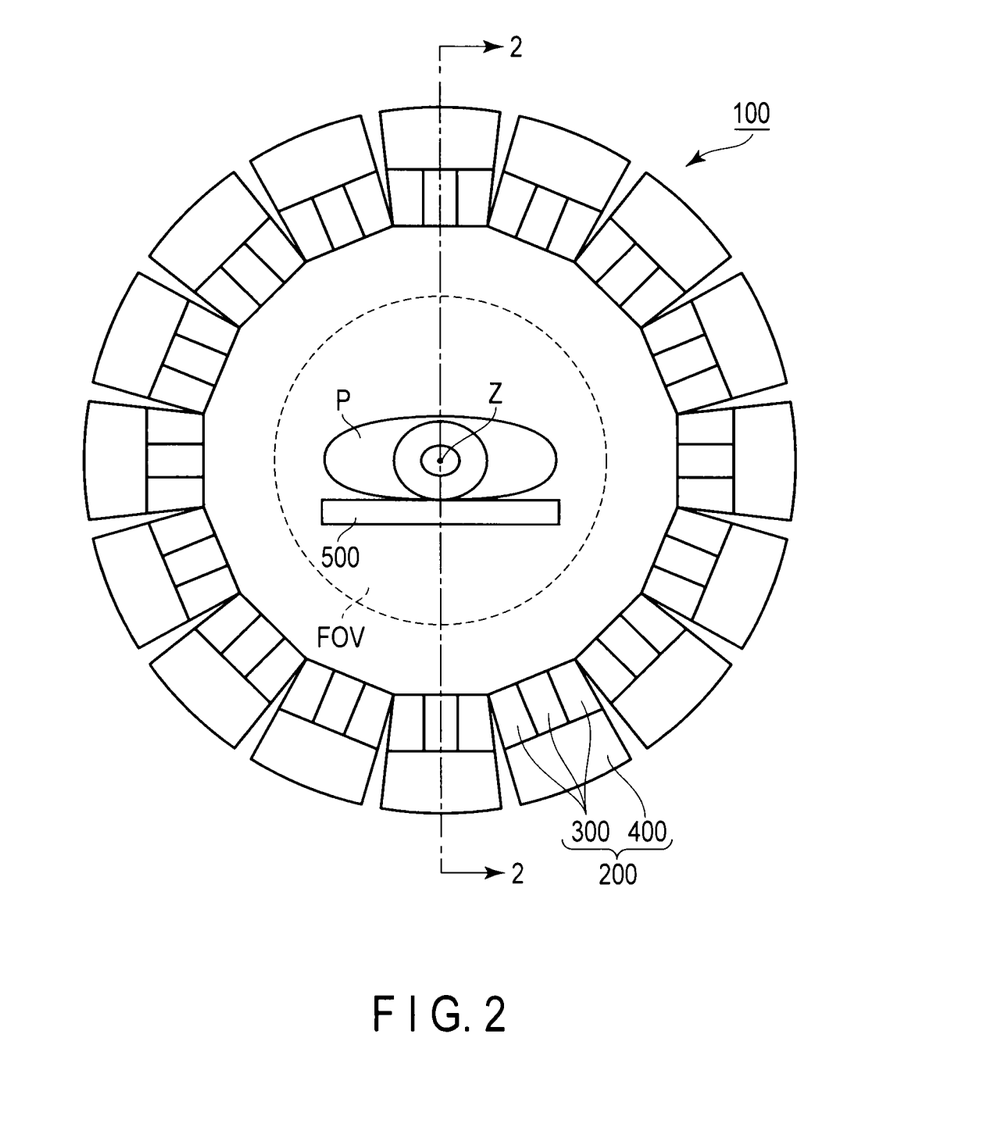
FIG. 2 is a schematic cross-sectional view of a detector ring mounted in a gantry in FIG. 1.
Figure 3:
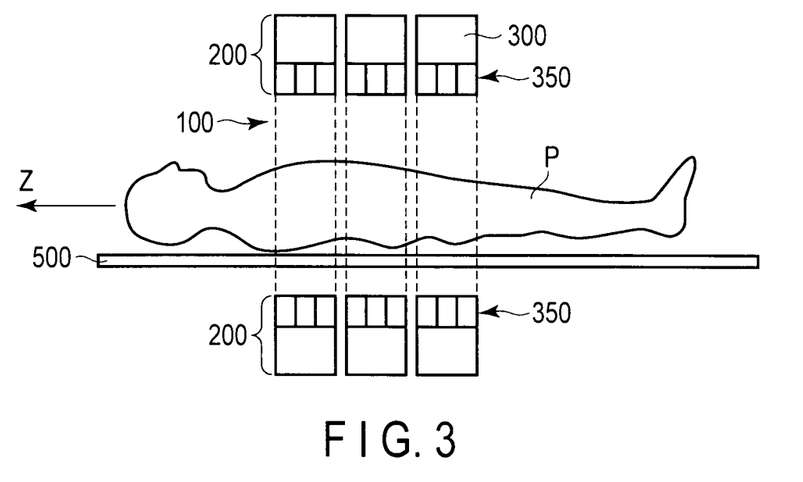
FIG. 3 is a schematic longitudinal sectional view of the detector ring in FIG. 2.

FIG. 2 is a schematic cross-sectional view of a detector ring 100 mounted in the gantry 20. FIG. 3 is a schematic longitudinal sectional view (2-2 section in FIG. 2) of the detector ring 100 in FIG. 2. The gantry 20 includes a plurality of detector rings 100 arranged along a central axis Z of a circumference. The detector ring 100 includes a plurality of detectors 200 arranged on the circumference around the central axis Z. An image field of view (FOV) is formed in an opening of the detector ring 100. A top 500 on which a subject P is placed is inserted through the opening of the detector ring 100 so that an imaging region of the subject P is within FOV. The subject P is placed on the top 500 so that the body axis thereof matches the central axis Z. A drug labeled with a radioisotope is injected into a subject P for PET imaging. The detector 200 detects pair annihilation gamma-rays emitted from inside the subject P to generate an electric signal in a pulse shape in accordance with the quantity of light of the detected pair annihilation gamma-rays.

More specifically, the detector 200 includes a plurality of scintillators 300 and a plurality of photomultipliers 400. The scintillator 300 generates scintillation upon receiving pair annihilation gamma-rays originating from a radioisotope inside the subject P. Each scintillator is arranged in such a way that the longitudinal direction of each scintillator substantially matches the radial direction of the detector ring. The photomultiplier 400 is provided at one end of the scintillator 300 regarding the radial direction perpendicular to the central axis Z. Typically, a light guide (not shown) is provided between the scintillator 300 and the photomultiplier 400. The plurality of scintillators 300 and the plurality of photomultipliers 400 contained in the detector ring 100 are arranged concentrically (in a concentric cylindrical shape). Scintillation generated by the scintillator 300 propagates through the scintillator 300 to reach the photomultiplier 400. The photomultiplier 400 generates an electric signal in a pulse shape in accordance with the quantity of light of scintillation. The generated electric signal is supplied to, as shown in FIG. 1, the signal processor 30.

The signal processor 30 generates single event data based on an electric signal from the photomultiplier 400. More specifically, the signal processor 30 performs detection time measurement processing, position calculation processing, and energy calculation processing. In the detection time measurement processing, the signal processor 30 measures the detection time of gamma-rays by the detector 200. More specifically, the signal processor 30 monitors the peak value of the electric signal from the photomultiplier 400. Then, the signal processor 30 measures the time when the peak value of the electric signal exceeds a preset threshold as the detection time. That is, the signal processor 30 electrically detects annihilation gamma-rays by detecting that the strength of the electric signal exceeds the threshold. In the position calculation processing, the signal processor 30 calculates an incident position of annihilation gamma-rays based on an electric signal from the photomultiplier 400. The incident position of annihilation gamma-rays corresponds to position coordinates of the scintillator 300 on which annihilation gamma-rays are incident. In the energy calculation processing, the signal processor 30 calculates an energy value of annihilation gamma-rays incident on the scintillator 300 based on an electric signal from the photomultiplier 400. Data of detection times, data of position coordinates, and data of energy values regarding single events are associated. A combination of data of energy values, data of position coordinates, and data of detection times regarding single events is called single event data. Single event data is successively generated each time annihilation gamma-rays are detected. The generated single event data is supplied to the coincidence counter 40.

The coincidence counter 40 performs coincidence counting processing on single event data on a plurality of single events. More specifically, the coincidence counter 40 repeatedly determines event data on two single events that fall within a preset time window among single event data that is repeatedly supplied. The time period is set to, for example, about 6 ns to 18 ns. Such a pair of single events is estimated to originate from pair annihilation gamma-rays generated from the same pair annihilation point. A pair of single events is called a coincidence event together. A line connecting a pair of the detectors 200 (more specifically, the scintillators 300) that detect the pair annihilation gamma-rays is called an LOR (line of response). In this manner, the coincidence counter 40 counts the coincidence events for each LOR. Event data on a pair of events constituting the LOR (hereinafter, referred to as coincidence event data) is stored in the storage 50.

The reconstruction unit 60 reconstructs image data that represents the spatial distribution of concentration of a radioisotope inside the subject based on coincidence event data on a plurality of coincidence events. The reconstruction unit 60 executes the reconstruction method (hereinafter, referred to as the TOF-PET reconstruction method) by using a detection time difference of a pair of annihilation gamma-rays. In the TOF-PET reconstruction method, the probability of presence of a pair annihilation point in each pixel on the LOR is different depending on the detection time difference of coincidence events.

Figure 4:
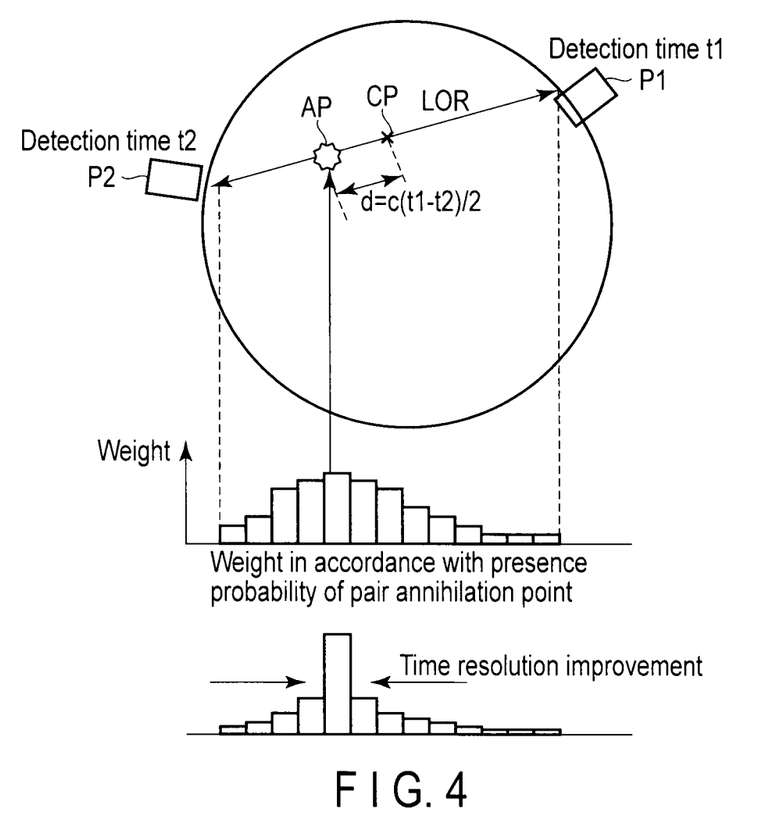
FIG. 4 is a diagram illustrating the principle of a TOF-PET reconstruction method used by a reconstruction unit in FIG. 1.

FIG. 4 is a diagram illustrating the principle of the TOF-PET reconstruction method. As shown in FIG. 4, it is assumed that a pair of annihilation gamma-rays is detected by a detector P1 at detection time t1 and by a detector P2 at detection time t2. In this case, a distance d from a center point CP of the LOR to a pair annihilation point AP is represented by Formula (1) below. c is the speed of light.

$$d=c(t1-t2)/2 \quad (1)$$

The reconstruction unit 60 uses Formula (1) to calculate the position of the pair annihilation point on the LOR for each coincidence event. The position of the LOR is calculated by the reconstruction unit 60 based on two detection positions of two events constituting the LOR. When the position of a pair annihilation point is calculated, the reconstruction unit 60 sets the weight in accordance with the probability of presence of the pair annihilation point for each pixel on the LOR. The weight of the target pixel is set so as to become smaller as the distance from the pair annihilation point increases. The higher the time resolution is, the higher the accuracy of the distribution of calculated pair annihilation point is. Thus, with a decreasing time resolution, a weight relatively higher than that of other pixels is set to the pixel of the calculated pair annihilation point. The reconstruction unit 60 uses the weight set in this manner to reconstruct image data from coincidence event data. For example, the reconstruction unit 60 generates projection data for PET representing the position of the LOR and the number of counts based on coincidence event data. Then, the reconstruction unit 60 generates image data from the generated projection data by using the TOF-PET reconstruction method. The reconstructed image data is supplied to the storage 50. Thus, the TOF-PET reconstruction method can improve, compared with a reconstruction method using no detection time difference, the signal-to-noise (S/N) ratio by using a detection time difference of coincidence events. That is, the time resolution is an important parameter in the TOF-PET reconstruction method.

The display 70 displays an image corresponding to image data in a display device. As a display device, a CRT display, liquid crystal display, organic EL display, or plasma display can appropriately be used.

The operation unit 80 receives various instructions by an operator via an input device or information input. As an input device, a keyboard, mouse, various buttons, or touch key panel can appropriately be used.

Next, the structure of the detector ring 100 according to the present embodiment will be described in detail.

As shown in FIG. 3, the gantry 20 is provided with a plurality of the detector rings 100 arranged along the Z axis. In FIG. 3, the three detector rings 100 are shown for illustration. Each of the detector rings 100 includes a plurality of scintillator rings 350 arranged along the Z axis. The scintillator ring 350 includes the plurality of scintillators 300 arranged along a substantial circumference around the Z axis.

In FIG. 3, the three scintillator rings 350 are shown for each of the detector rings 100 for illustration. Hereinafter, the number of all the scintillator rings 350 contained in the plurality of detector rings arranged in the central axis Z will be called the number of columns. In the case of FIG. 3, the number of columns of the scintillator rings 350, that is, the number of columns of the scintillators 300 is 9. All the scintillators 300 contained in the gantry 20 will be called a scintillator group 360. Incidentally, the number of columns of the scintillator rings 350 (the number of columns of the scintillators 300), the number of the detectors 200 in the detector ring 100, and the number of the scintillators 300 in the detector 200 are not limited to those shown in FIG. 3.

In the detector 200, the plurality of scintillators 300 is arranged, for example, two-dimensionally. The scintillator 300 according to the present embodiment may be formed from any kind of known scintillator material. For example, the scintillator 300 may be formed from scintillator materials such as NaI (sodium iodide), BGO (bismuth germanium oxide), LSO (obtained by adding a fixed amount of cerium to lutetium silicate), LaBr3:Ce, and LYSO (mixed crystal of LSO and yttrium silicate). A lutetium crystal is frequently used as the material of the scintillator 300. In addition to the above materials, the scintillator 300 may be formed from, for example, a gallium base crystal or garnet base crystal.

Next, the relationship among the scintillator 300, manufacturing costs, and image quality will be described.

Typically, the image quality improves with an increase in detection efficiency of pair annihilation gamma-rays. Main determination factors of image quality include the total number of counts of coincidence events and time resolution. Factors of a PET apparatus that determine the total number of counts of coincidence events include sensitivity of the PET apparatus and detection efficiency of the scintillator.

The sensitivity will be described below. As described above, pair annihilation gamma-rays are emitted from a subject. Of these pair annihilation gamma-rays, some are detected by detectors of a PET apparatus and others are not detected. The sensitivity is the ratio of pair annihilation gamma-rays that can be detected by detectors of the PET apparatus to the total number of pair annihilation gamma-rays.

Next, the detection efficiency of the scintillator will be described. When a gamma-ray is incident on the scintillator, the gamma-ray causes an interaction with the scintillator with a fixed probability in accordance with the scintillator material or incident scintillator energy to emit light. If no interaction is caused, the gamma-ray passes through the scintillator. In this case, the detection efficiency of the scintillator is the probability with which the interaction is caused.

According to physical properties of the scintillator, the probability of a gamma-ray interacting with the scintillator improves with an increasing length of the scintillator along the radial direction of the detector ring, thus improving detection efficiency of the scintillator with regard to gamma-rays. Hereinafter, the length of the scintillator along the radial direction of the detector ring will be called simply the thickness. As described above, the detection efficiency of the scintillator is defined as the ratio of the number of annihilation gamma-rays that have interacted with the scintillator to the number of annihilation gamma-rays incident on the scintillator. In the past, the thickness of the scintillator is determined by taking the mean free path into consideration to obtain adequate detection efficiency. Thus, the thickness of the scintillator is typically set to a thickness exceeding 20 mm.

With an increasing thickness of the scintillator, the total scintillator volume inside the gantry increases. On the other hand, the scintillator is expensive. Therefore, with an increase in thickness of the scintillator, manufacturing costs of the TOF-PET apparatus 1 increase.

Scintillation is generated by an interaction between annihilation gamma-rays and the scintillator. Scintillation propagates through the scintillator to reach a photomultiplier. In this case, the scintillation is randomly reflected inside the scintillator. Due to the random reflection, energy of the scintillation is attenuated. The position of interaction between annihilation gamma-rays and the scintillator (that is, the generation position of scintillation) inside the scintillator varies more with an increasing thickness of the scintillator. With an increase in variations of the interaction position, variations in the number of times of random reflection of scintillation increase, leading to deterioration in time resolution of the TOF-PET apparatus 1.

That is, the probability of interaction increases with an increasing thickness of the scintillator so that detection efficiency of the scintillator increases, but manufacturing costs rise, resulting in deterioration in time resolution.

Under conditions of a fixed thickness of the scintillator, increasing the number of columns of the scintillator can be considered to improve sensitivity of the PET apparatus. However, increasing the thickness of the scintillator or the number of columns of the scintillator leads to an increase in the total volume of a scintillator group in the gantry. Therefore, manufacturing costs of the TOF-PET apparatus 1 rise with an increasing number of columns of the scintillator.

The thickness of the scintillator 300 according to the present embodiment is set based on the idea of realizing the optimal balance between manufacturing costs and image quality in the TOF-PET apparatus. In the present embodiment, the image quality is evaluated based on the value obtained by dividing the total number of counts of coincidence events of pair annihilation gamma-rays by the time resolution. The reason therefor is as described below. For the sake of simplicity, the value obtained by dividing the total number of counts of coincidence events of pair annihilation gamma-rays by the time resolution is called simply as the total number of counts/time resolution in the description that follows. The TOF-PET reconstruction method uses a detection time difference and so is, compared with a reconstruction method of a non-TOF-PET apparatus that does not use a detection time difference, more subject to the time resolution. Thus, the number of counts is not sufficient for the evaluation of image quality of the TOF-PET apparatus 1 and the time resolution is required. The signal-to-noise (S/N) ratio, which is a parameter of the image quality, is proportional to the square root of the total number of counts of coincidence events of pair annihilation gamma-rays and is inversely proportional to the time resolution. The total number of counts/time resolution is a value obtained by dividing the total number of counts of coincidence events of pair annihilation gamma-rays counted by the scintillator by the specific time resolution in accordance with the thickness of the scintillator.

The inventors performed a simulation using the thickness of the scintillator as a parameter under conditions of the fixed total volume of scintillators contained in a scintillator group while being aware of sensitivity of the PET apparatus. A standard scintillator of a non-TOF-PET apparatus is used as a reference scintillator to be compared with. A scintillator whose probability of interaction with annihilation gamma-rays is 80% is set as the reference scintillator.

The scintillator simulation will be described below by citing a concrete example of an LYSO scintillator. The standard thickness of the scintillator of a conventional PET apparatus is set to the range of 20 mm to 26 mm in consideration of the probability of interaction regardless of the composition of scintillator. That is, if the thickness of the LYSO scintillator is 24 mm or more, substantially 80% of annihilation gamma-rays incident on the LYSO scintillator are detectable. In other words, the probability of interaction of the LYSO scintillator whose thickness is 24 mm or more is 80% or more. Based on this rule of thumb, the thickness of the reference scintillator of an LYSO scintillator in the present embodiment is assumed to be 24 mm.

Figure 5:
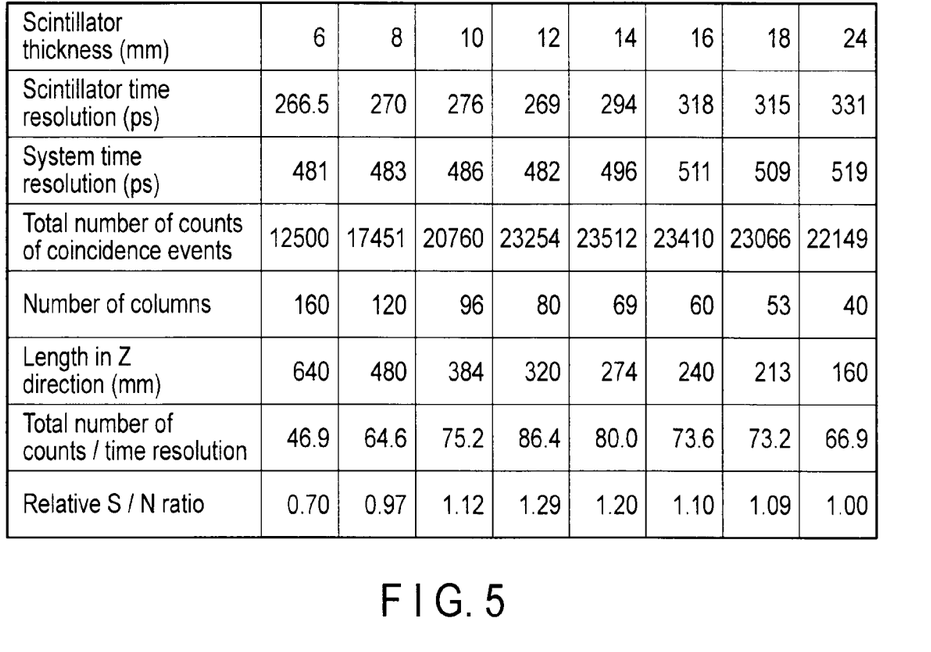
FIG. 5 is a diagram exemplifying a simulation result of an LYSO scintillator according to the present embodiment.
Figure 6:
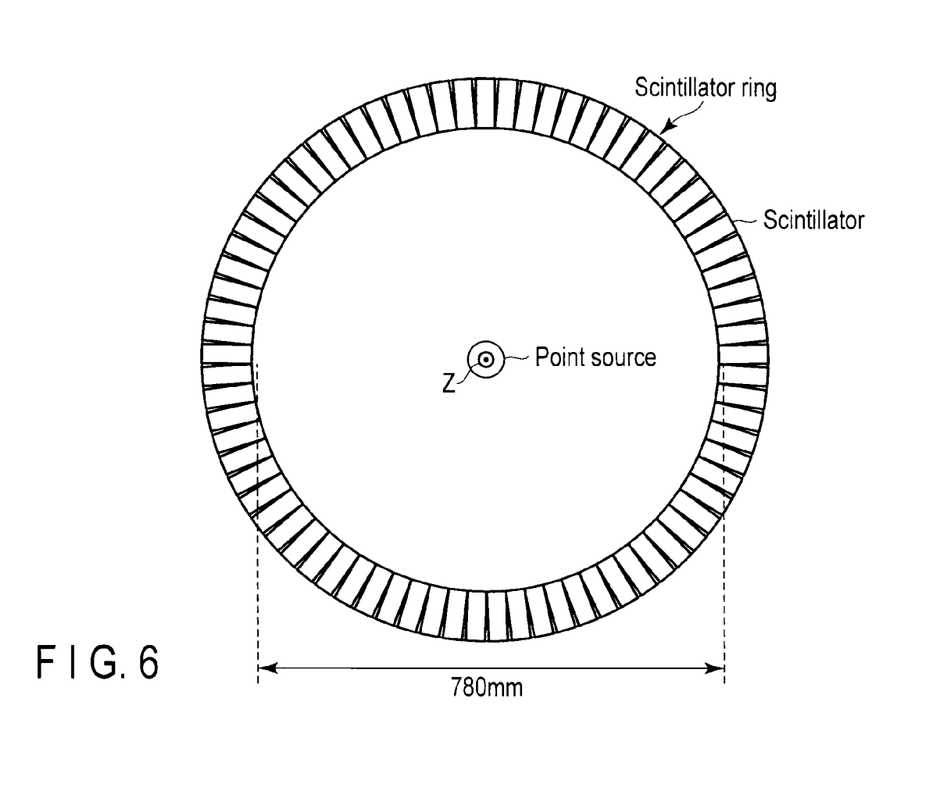
FIG. 6 is a diagram showing a geometry in the simulation shown in FIG. 5.

FIG. 5 is a diagram exemplifying a simulation result of the LYSO scintillator. FIG. 6 is a diagram showing a geometry in the simulation shown in FIG. 5. The simulation in FIG. 5 shows various parameters of the scintillator when the thickness of the scintillator and the number of columns are changed while the total volume of the scintillators is maintained constant. Parameters include the thickness [mm], scintillator time resolution [ps], system time resolution [ps], total number of counts of coincidence events, number of columns, length of a scintillator group along the Z axis direction (length in the Z direction) [mm], total number of counts/time resolution, and relative S/N ratio. The scintillator time resolution is a time resolution of a scintillator alone.

In this simulation, as shown in FIG. 6, a point source is arranged in the center of FOV and a plurality of scintillators is arranged around the point source in a ring shape. The diameter of the scintillator ring is set to 780 mm with the point source as the center thereof. Also in the simulation in FIG. 5, the length of each scintillator along the Z axis is set to 4 mm.

Here, the reason for maintaining the total volume of scintillators constant while sensitivity of the PET apparatus being considered will be described.

Figure 7:
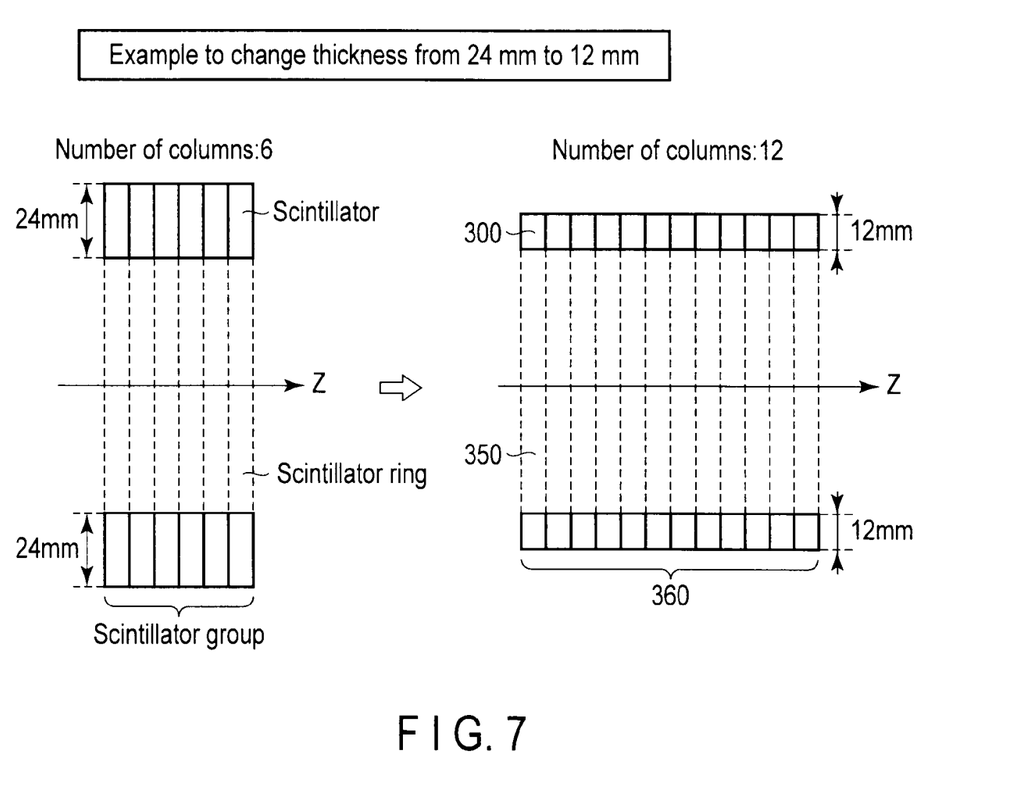
FIG. 7 is a diagram showing an arrangement example of scintillators to illustrate the simulation in FIG. 5.
Figure 8:
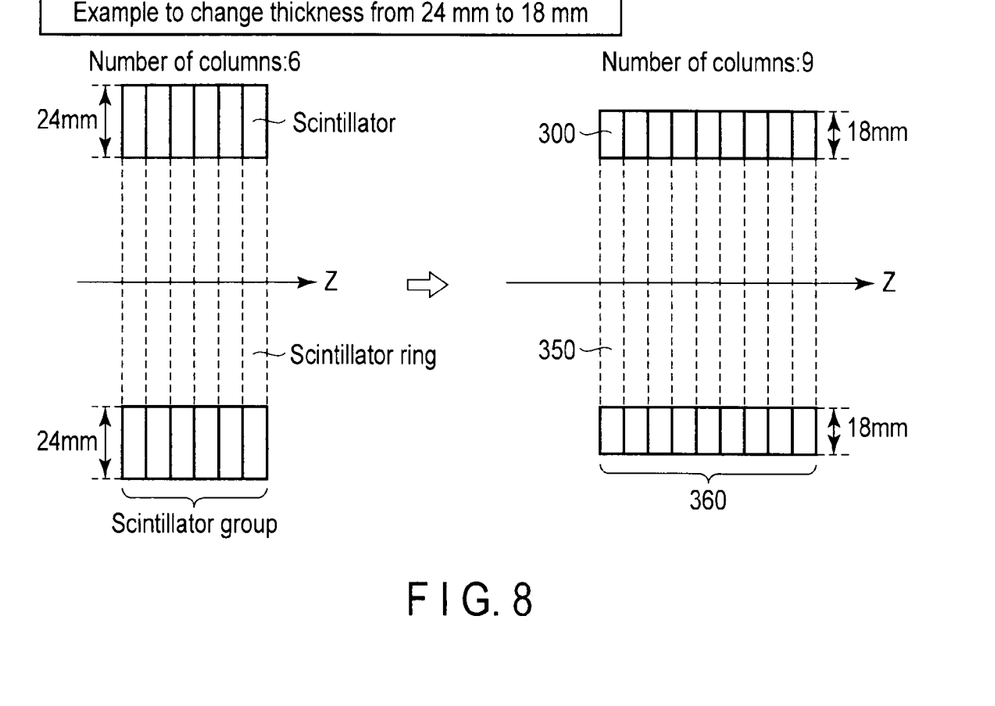
FIG. 8 is a diagram showing another arrangement example of scintillators to illustrate the simulation in FIG. 5.

FIGS. 7 and 8 are diagrams showing an increase in the number of columns with a decreasing thickness of the scintillator. FIG. 7 shows an example in which the thickness of the scintillator is changed from the reference thickness 24 mm to 12 mm (½ of 24 mm). FIG. 8 shows an example in which the thickness of the scintillator 300 is changed from the reference thickness 24 mm to 18 mm (⅔ of 24 mm). When the time resolution should be improved, it is better for the scintillator to be thinner. However, if the scintillator is simply made thinner, detection efficiency of the scintillator declines, which reduces the number of counts by the detector and decreases sensitivity of the PET apparatus. The solid angle involved in detection of annihilation gamma-rays is increased (the FOV size in the Z axis direction is increased) by increasing the number of columns of scintillator. Thus, to make the scintillator thinner while suppressing a decrease in sensitivity of the PET apparatus, the number of columns of scintillator may be increased.

More specifically, in the case of FIG. 7, the thickness of the scintillator is changed from 24 mm to 12 mm and the number of columns is changed from 6 to 12. In the case of FIG. 8, the thickness of the scintillator is changed from 24 mm to 18 mm and the number of columns is changed from 6 to 9. Thus, it is necessary to increase the number of columns with a decreasing thickness to prevent decreased sensitivity of the PET apparatus. That is, if the time resolution should be improved while decreased sensitivity of the PET apparatus being prevented, it is necessary to increase the number of columns of scintillator while the thickness of the scintillator being reduced. In other words, if the time resolution should be improved while decreased sensitivity of the PET apparatus being prevented, it is necessary to reduce the thickness of the scintillator while the total volume being maintained constant. By maintaining the total volume of scintillators constant, manufacturing costs of the TOF-PET apparatus are maintained.

As a result of examining the simulation result shown in FIG. 5, the inventors found the presence of a thickness range in which the total number of counts/time resolution, which is an index showing the image quality of a PET apparatus, is improved more than that of the reference scintillator when the thickness and the number of columns are changed under conditions of a fixed total volume of scintillators.

As shown in FIG. 5, values of the total number of counts/time resolution are shown in the field of the total number of counts/time resolution when the thickness and the number of columns are changed under conditions of a fixed total volume of scintillators. The value of the total number of counts/time resolution of the reference scintillator is 66.9. Thus, if the value of the total number of counts/time resolution of an LYSO scintillator is larger than 66.9, the image quality of the LYSO scintillator is better than that of the reference scintillator. The thickness of 10 mm to 18 mm in FIG. 5 is now focused on. If the thickness is between 10 mm and 18 mm, the value of the total number of counts/time resolution is larger than 66.9. This thickness range is shorter than the thickness (24 mm) of the reference scintillator set in consideration of the mean free path of annihilation gamma-rays. That is, in the simulation shown in FIG. 5, a scintillator having the thickness of 10 mm to 18 mm has a better time resolution than the reference scintillator having the thickness of 24 mm. Since the total volume is constant in the simulation of FIG. 5, a scintillator having the thickness of 10 mm to 18 mm will not suffer extreme deterioration in the total number of counts of coincidence events compared with the reference scintillator. That is, if the image quality should be improved more than that of the reference scintillator while manufacturing costs being maintained at the same level as those of the reference scintillator, the thickness of the scintillator 300 according to the present embodiment may be set to any value between 10 mm and 18 mm.

As described above, the LYSO scintillator is used for the simulation shown in FIG. 5. Characteristics of a scintillator differ depending on the composition of the scintillator. However, the tendency of change of various parameters with regard to the thickness shows the same tendency regardless of the composition of the scintillator. That is, regardless of the composition of the scintillator, a thickness range in which the value of the total number of counts/time resolution is more improved than that of the reference scintillator is present.

This is because the time resolution that is not considered in the past is considered for the setting of the thickness of the scintillator. That is, to optimize the image quality of a TOF-PET apparatus in which the priority of time resolution is high, it is better to increase the number of columns of scintillators and use scintillators whose thickness is thinner than that of the reference scintillator used in a non-TOF-PET apparatus to maintain the number of counts.

Based on the above consideration, when the thickness of the scintillator 300 and the number of columns are changed so that the total volume of the scintillator group 360 is kept constant, the thickness of the scintillator 300 according to the present embodiment is set to the thickness range in which the value of the total number of counts/time resolution is more improved than that of the reference scintillator. In this case, the ratio of the value of the total number of counts/time resolution of the scintillator group 360 using the scintillator 300 according to the present embodiment to the value of the total number of counts/time resolution of a scintillator group using the reference scintillator is larger than 1. Accordingly, the TOF-PET apparatus 1 according to the present embodiment can maintain manufacturing costs of a conventional TOF-PET apparatus using the reference scintillator and also improve the image quality when compared with the conventional TOF-PET apparatus.

If the total volume of scintillators is constant and the scintillator 300 is made thinner than the reference scintillator, the number of columns of the scintillator 300 (the scintillator ring 350) increases. Therefore, the FOV size along the Z axis direction of the TOF-PET apparatus 1 according to the present embodiment is increased when compared with an apparatus including the reference scintillator.

Figure 9:
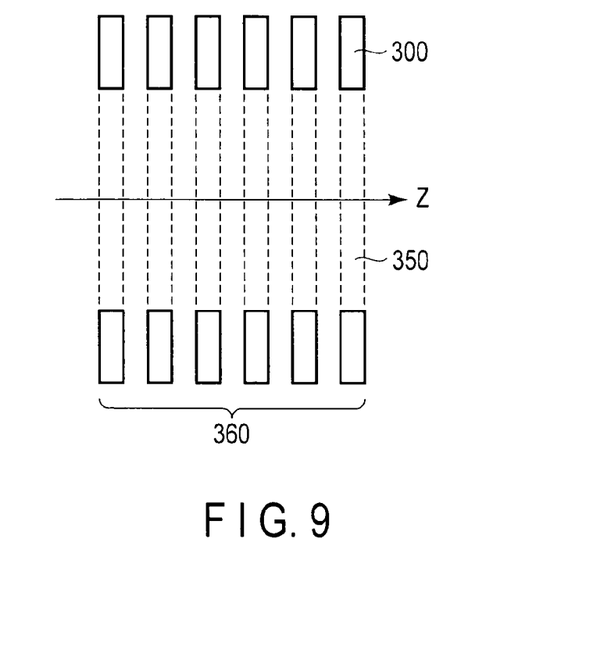
FIG. 9 is a diagram showing still another arrangement example of scintillators according to the present embodiment.

In the simulation result shown in FIG. 5, the number of columns may be insufficient as the FOV size for dynamic imaging in a range in which the scintillator 300 is relatively thick. In this case, as shown in FIG. 9, a plurality of the scintillator rings 350 may be arranged by being spaced therebetween along the Z axis to increase the FOV size along the Z axis. By arranging the plurality of the scintillators 300 along the Z axis by being spaced therebetween in this manner, the FOV size along the Z axis can be increased while the number of columns of the scintillator ring 350 being increased and a rise in manufacturing costs being suppressed. Therefore, a FOV size sufficient for dynamic imaging that requires a large FOV size can be realized while the number of columns being increased and a rise in manufacturing costs being suppressed.

According to the TOF-PET apparatus 1 in the present embodiment, manufacturing costs can be reduced while the conventional image quality being maintained. If, for example, the value of the total number of counts/time resolution according to the present embodiment is fixed to the value of the total number of counts/time resolution of the reference scintillator, the thickness of the scintillator according to the present embodiment may be set to a range of the thickness thinner than the reference thickness. For an LYSO scintillator having the thickness of, for example, as shown in FIG. 7, 12 mm, the value of the total number of counts/time resolution is 86.4. For an LYSO scintillator having the reference thickness of 24 mm, on the other hand, the value of the total number of counts/time resolution is 66.9. The value of the total number of counts/time resolution deteriorates with a decreasing total volume of scintillators. That is, to change the value of the total number of counts/time resolution from 86.4 to 66.9, the LYSO scintillator can be made still thinner or the number of columns of scintillators can be reduced so that manufacturing costs can be reduced while the conventional image quality being maintained.

In recent years, detector rings having a relatively large inside diameter are desired for the purpose of imaging a large subject, preventing a pileup, or reducing a sense of oppression by a gantry on a subject. However, an increased amount of scintillator is unavoidable to manufacture gantries having a large opening. As described above, the TOF-PET apparatus 1 according to the present embodiment can implement substantially the same image quality as a conventional apparatus by using, compared with the conventional apparatus, a smaller amount of scintillator. Therefore, according to the present embodiment, gantries having a large opening can be provided at a lower price than the conventional apparatus.

As described above, the TOF-PET apparatus 1 according to the present embodiment acquires a high level of flexibility of setting by considering not only, like a conventional apparatus, the mean free path (probability of interaction), but also the time resolution for scintillator settings. Therefore, according to the present embodiment, the image quality and manufacturing costs can be optimized in accordance with preferences of the user or the like.

Figure 10:
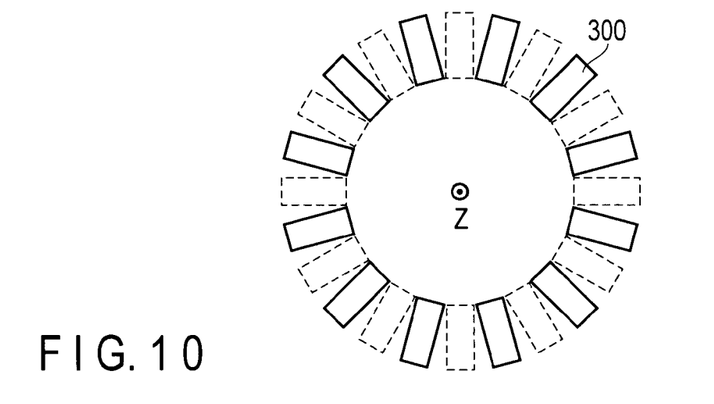
FIG. 10 is a diagram showing still another arrangement example of scintillators according to the present embodiment.
Figure 11:
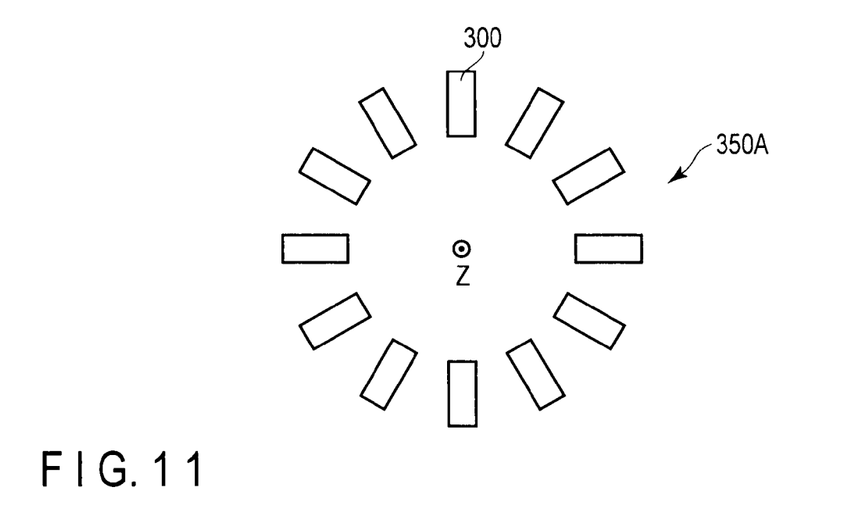
FIG. 11 is a diagram showing a scintillator ring 350A in FIG. 10.
Figure 12:
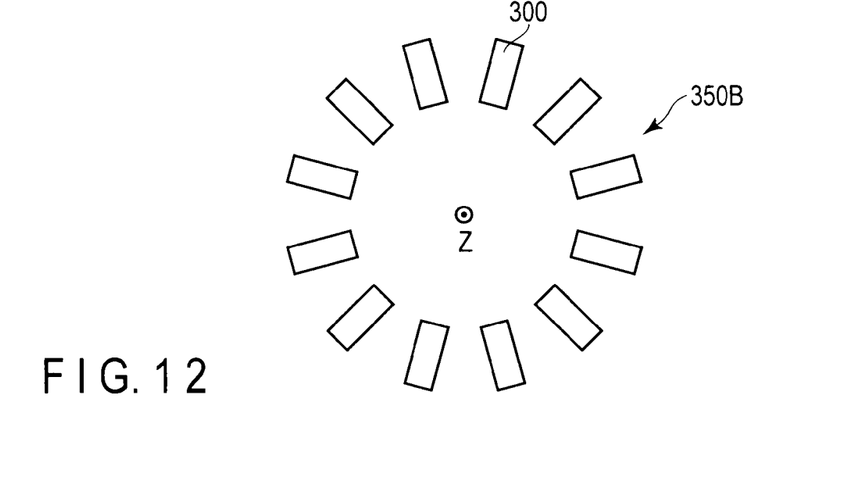
FIG. 12 is a diagram showing a scintillator ring 350B in FIG. 10.

The action to increase the FOV size along the Z axis direction is not limited to the arrangement example in FIG. 9. FIGS. 10, 11, and 12 are diagrams showing other arrangement examples of the scintillators 300 according to the present embodiment. FIGS. 10, 11, and 12 show states when the scintillators 300 are viewed from the same direction as in FIG. 2. FIG. 10 is a projection view of the scintillator ring 350A in FIG. 11 and the scintillator ring 350B in FIG. 12. As shown in FIG. 11, the scintillator ring 350A includes a plurality of the scintillators 300 arranged by being spaced therebetween on a substantial circumference. As shown in FIG. 12, the scintillator ring 350B includes a plurality of the scintillators 300 arranged by being spaced therebetween on a substantial circumference. The scintillator ring 350A and the scintillator ring 350B are arranged alternately along the Z axis. The scintillator ring 350A and the scintillator ring 350B are arranged alternately along the Z axis so that spacing between the scintillators 300 of the single scintillator rings 350A and 350B when viewed from the Z axis direction is filled. According to this arrangement example, the FOV size along the Z axis can be increased while manufacturing costs are maintained.

When the thickness of the scintillator 300 and the number of columns are changed so that the total volume of the scintillators 300 contained in the gantry 20 is maintained constant, as described above, the thickness of the scintillator 300 used in the TOF-PET apparatus 1 according to the present embodiment is set to a thickness range in which the value of the total number of counts/time resolution is more improved than that of the reference scintillator. That is, the thickness of the scintillator 300 is set to a value that takes not only the probability of interaction with annihilation gamma-rays, but also the time resolution into consideration. Accordingly, the TOF-PET apparatus 1 can provide a satisfactory time resolution even if the scintillator 300 whose thickness is thinner than that of the reference scintillator is included. In the past, the time resolution has been improved by upgrading a frontend circuit. In the present embodiment, however, the improvement of time resolution is realized by making the scintillator 300 thinner. Accordingly, the TOF-PET apparatus 1 can improve the image quality when compared with a conventional apparatus using the reference scintillator while maintaining the same manufacturing costs as those of the conventional apparatus.

Moreover, manufacturing costs of the TOF-PET apparatus 1 can be made lower than those of the conventional apparatus while the image quality of the conventional apparatus being maintained. Further, if the TOF-PET apparatus 1 according to the present embodiment has the image quality equivalent to that of the conventional apparatus, the examination time can be shortened compared with the conventional apparatus so that the number of patients who can be diagnosed per day can be increased. Moreover, the TOF-PET apparatus according to the present embodiment is more appropriate for dynamic imaging because the examination time is shortened compared with the conventional apparatus.

Thus, according to the present embodiment, the TOF-PET apparatus 1 that realizes the optimal balance between manufacturing costs and the image quality in the TOF-PET apparatus, the detector ring 100, and the detector 200 can be provided.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A TOF-PET apparatus comprising a plurality of detector rings arranged along a central axis thereof,
wherein each of the detector rings comprises:
a plurality of scintillators that are arranged on a substantial circumference around the central axis and generate scintillation in response to pair annihilation gamma-rays from a subject; and
a plurality of photomultipliers that generate an electric signal in accordance with the generated scintillation, and
a length of each of the scintillators along a radial direction of the substantial circumference is set to a range in which a value of a total number of counts/time resolution of coincidence events of pair annihilation gamma-rays is improved compared to a reference scintillator whose probability of interaction with pair annihilation gamma-rays is adjusted to 80% is used under conditions of a constant total volume of the scintillators.

2. The TOF-PET apparatus according to claim 1, wherein a ratio of the value of the total number of counts/time resolution of the coincidence events of the pair annihilation gamma-rays of each of the scintillators to the value of the total number of counts/time resolution of the coincidence events of the pair annihilation gamma-rays when the reference scintillator is used is larger than 1.

3. The TOF-PET apparatus according to claim 1, wherein when LYSO is used as a material of the scintillators, the length of each of the scintillators along the radial direction of the substantial circumference has any value in the range of 10 mm to 18 mM.

4. The TOF-PET apparatus according to claim 1, wherein each of the detector rings includes a plurality of scintillator rings arranged along the central axis, and
the scintillator rings are arranged by being spaced therebetween along the central axis.

5. The TOF-PET apparatus according to claim 1, wherein each of the detector rings includes a first scintillator ring and a second scintillator ring arranged along the central axis,
the first scintillator ring includes the scintillators arranged on the substantial circumference around the central axis by being spaced from each other,
the second scintillator ring includes the scintillators arranged on the substantial circumference around the central axis by being spaced from each other, and
the first scintillator ring and the second scintillator ring are alternately arranged so that the spacing is filled when viewed along the central axis.

6. A detector ring comprising:
a plurality of scintillators that are arranged on a substantial circumference around a central axis and generate scintillation in response to pair annihilation gamma-rays from a subject; and
a plurality of photomultipliers that generate an electric signal in accordance with the generated scintillation,
wherein a length of each of the scintillators along a radial direction of the substantial circumference is set to a range in which a value of a total number of counts/time resolution of coincidence events of pair annihilation gamma-rays is improved compared to a reference scintillator whose probability of interaction with pair annihilation gamma-rays is adjusted to 80% is used under conditions of a constant total volume of the scintillators.

7. The detector ring according to claim 6, wherein a ratio of the value of the total number of counts/time resolution of the coincidence events of the pair annihilation gamma-rays of each of the scintillators to the value of the total number of counts/time resolution of the coincidence events of the pair annihilation gamma-rays when the reference scintillator is used is larger than 1.

8. The detector ring according to claim 6, wherein when LYSO is used as a material of the scintillators, the length of each of the scintillators along the radial direction of the substantial circumference has any value in the range of 10 mm to 18 mm.

9. A detector comprising:
a plurality of scintillators that generate scintillation in response to annihilation gamma-rays from a subject; and
a plurality of photomultipliers that generate an electric signal in accordance with the generated scintillation,
wherein a length of each of the scintillators along a longitudinal direction is set to a range in which a value of a total number of counts/time resolution of coincidence events of pair annihilation gamma-rays is improved compared to a reference scintillator whose probability of interaction with pair annihilation gamma-rays is adjusted to 80% is used under conditions of a constant total volume of the scintillators.

10. The detector according to claim 9, wherein a ratio of the value of the total number of counts/time resolution of the coincidence events of the pair annihilation gamma-rays of each of the scintillators to the value of the total number of counts/time resolution of the coincidence events of the pair annihilation gamma-rays when the reference scintillator is used is larger than 1.

11. The detector according to claim 9, wherein when LYSO is used as a material of the scintillators, the length of each of the scintillators along the longitudinal direction has any value in the range of 10 mm to 18 mm.

* * * * *